(12) United States Patent
Guo et al.

(10) Patent No.: US 6,479,242 B1
(45) Date of Patent: Nov. 12, 2002

(54) METHOD FOR GENOTYPING OF SINGLE NUCLEOTIDE POLYMORPHISM

(75) Inventors: Baochuan Guo, Solon; Xiyuan Sun, Cleveland, both of OH (US)

(73) Assignee: Cleveland State University, Cleveland, OH (US)

( * ) Notice: Subject to any disclaimer, the term of this patent is extended or adjusted under 35 U.S.C. 154(b) by 0 days.

(21) Appl. No.: 09/698,505

(22) Filed: Oct. 27, 2000

(51) Int. Cl.⁷ .............................. C12Q 1/68; C12P 19/34
(52) U.S. Cl. ........................................... 435/6; 435/91.2
(58) Field of Search .................... 435/6, 91.2; 536/22.1

(56) References Cited

U.S. PATENT DOCUMENTS

| | | | |
|---|---|---|---|
| 5,605,798 A | 2/1997 | Koster | |
| 5,691,141 A | 11/1997 | Koster | |
| 5,885,775 A | 3/1999 | Haff et al. | |
| 5,965,363 A | 10/1999 | Monforte et al. | |
| 6,043,031 A | * 3/2000 | Koster et al. | 435/6 |

OTHER PUBLICATIONS

"A New MALDI–TOF based mini–sequencing assay for genotyping of SNPS" by Sun, et al., *Nucleic Acids Research*, 2000, vol. 28, No. 12.
Ausubel FM et al. DNA sequencing. Short Protocols in Molecular Biology. 4th edition, p. 7–1 to 7–4, 1999.*
Sun X et al. A new MALDI–TOF based mini–sequencing assay for genotyping of SNPs. Nucleic Acids Res., 28(12), E68 i–viii, 2000.*

* cited by examiner

*Primary Examiner*—Eggerton A. Campbell
*Assistant Examiner*—Suryaprabha Chunduru
(74) *Attorney, Agent, or Firm*—Calfee, Halter & Griswold LLP

(57) ABSTRACT

The VSET method comprises: providing a polynucleotide acid sample comprising at least one target site, and a first region of nucleotides immediately adjacent to the target site; preferably genomic DNA; preferably amplifying the polynucleotide; then combining the polynucleotide sample with: three dideoxynucletides selected from the group of ddGTP, ddATP, ddCTP, and ddTTP; and one deoxynucleotide selected from the group consisting of and dGTP, dATP, dCTP, and dTTP wherein the nucleotide of the deoxynucleotide is not the same as the nucleotide in the dideoxynulceotide; and a mini-sequencing primer complementary to the first region of nucleotides; extending the mini-sequencing primer with a dideoxynucletide or deoxynulceotide whose base is complementary to the base at the target site, to provide extension products; and then identifying the extension products, preferably by (MALDI-TOF) mass spectrometry. One of the three ddNTps is complementary to one of the allelic variations at the single point mutation site while the deoxynucleotide is complementary to the other allelic variant at the single point mutation site. The mini-sequencing primer hybridizes to a polynucleotide sequence immediately next to a single point mutation site and is extended by the DNA polymerases. The genotype at the variable site is determined on the basis of the number of nucleotides contained in the extension products.

27 Claims, 9 Drawing Sheets

SEQUENCE LISTING

<160> NUMBER OF SEQ ID NOS: 47

<210> SEQ ID NO 1
<211> LENGTH: 31
<212> TYPE: DNA
<213> ORGANISM: A Homozygote

<400> SEQUENCE: 1
tagcagttcc gtgagaacgg atgcggtagt c                          31

<210> SEQ ID NO 2
<211> LENGTH: 23
<212> TYPE: DNA
<213> ORGANISM: A Homozygote

<400> SEQUENCE: 2
tcaaggcact cttgcctacg cca                                   23

<210> SEQ ID NO 3
<211> LENGTH: 27
<212> TYPE: DNA
<213> ORGANISM: A Homozygote

<400> SEQUENCE: 3
tcaaggcact cttgcctacg ccatddc                               27

<210> SEQ ID NO 4
<211> LENGTH: 31
<212> TYPE: DNA
<213> ORGANISM: G Homozygote

<400> SEQUENCE: 4
tagcagttcc gtgagaacgg atgcggtggt c                          31

<210> SEQ ID NO 5
<211> LENGTH: 23
<212> TYPE: DNA
<213> ORGANISM: G Homozygote

```
<400> SEQUENCE: 5
tcaaggcact cttgcctacg cca                                          23

<210> SEQ ID NO 6
<211> LENGTH: 26
<212> TYPE: DNA
<213> ORGANISM: G Homozygote

<400> SEQUENCE: 6
tcaaggcact cttgcctacg ccaddc                                       26

<210> SEQ ID NO 7
<211> LENGTH: 31
<212> TYPE: DNA
<213> ORGANISM: A/G Heterozygote

<400> SEQUENCE: 7
tagcagttcc gtgagaacgg atgcggtggt c                                 31

<210> SEQ ID NO 8
<211> LENGTH: 23
<212> TYPE: DNA
<213> ORGANISM: A/G Heterozygote

<400> SEQUENCE: 8
tcaaggcact cttgcctacg cca                                          23

<210> SEQ ID NO 9
<211> LENGTH: 27
<212> TYPE: DNA
<213> ORGANISM: A/G Heterozygote

<400> SEQUENCE: 9
tcaaggcact cttgcctacg ccacddc                                      27

<210> SEQ ID NO 10
<211> LENGTH: 27
<212> TYPE: DNA
<213> ORGANISM: A/G Heterozygote

<400> SEQUENCE: 10
tcaaggcact cttgcctacg ccatddc                                      27

<210> SEQ ID NO 11
<211> LENGTH: 32
<212> TYPE: DNA
<213> ORGANISM: G Homozygote

<400> SEQUENCE: 11
acattctcgt ctagggacct gtccgctcct ta                                32

<210> SEQ ID NO 12
<211> LENGTH: 18
<212> TYPE: DNA
<213> ORGANISM: G Homozygote

<400> SEQUENCE: 12
gcagatccct ggacaggc                                                18

<210> SEQ ID NO 13
<211> LENGTH: 23
<212> TYPE: DNA
<213> ORGANISM: G Homozygote
```

<400> SEQUENCE: 13
gcagatccct ggacaggcdg dda    23

<210> SEQ ID NO 14
<211> LENGTH: 32
<212> TYPE: DNA
<213> ORGANISM: A Homozygote

<400> SEQUENCE: 14
acattctcgt ctagggacct gtccgttcct ta    32

<210> SEQ ID NO 15
<211> LENGTH: 18
<212> TYPE: DNA
<213> ORGANISM: A Homozygote

<400> SEQUENCE: 15
gcagatccct ggacaggc    18

<210> SEQ ID NO 16
<211> LENGTH: 21
<212> TYPE: DNA
<213> ORGANISM: A Homozygote

<400> SEQUENCE: 16
gcagatccct ggacaggcdd a    21

<210> SEQ ID NO 17
<211> LENGTH: 32
<212> TYPE: DNA
<213> ORGANISM: A/G Heterozygote

<400> SEQUENCE: 17
acattctcgt ctagggacct gtccgttcct ta    32

<210> SEQ ID NO 18
<211> LENGTH: 18
<212> TYPE: DNA
<213> ORGANISM: A/G Heterozygote

<400> SEQUENCE: 18
gcagatccct ggacaggc    18

<210> SEQ ID NO 19
<211> LENGTH: 21
<212> TYPE: DNA
<213> ORGANISM: A/G Heterozygote

<400> SEQUENCE: 19
gcagatccct ggacaggcdd a    21

<210> SEQ ID NO 20
<211> LENGTH: 23
<212> TYPE: DNA
<213> ORGANISM: A/G Heterozygote

<400> SEQUENCE: 20
gcagatccct ggacaggcdg dda    23

<210> SEQ ID NO 21
<211> LENGTH: 45
<212> TYPE: DNA

-continued

<213> ORGANISM: A Homozygote

<400> SEQUENCE: 21
ttataaggcc tgctgaaaat gactgaatat aaacttgtgg tagtt        45

<210> SEQ ID NO 22
<211> LENGTH: 35
<212> TYPE: DNA
<213> ORGANISM: A Homozygote

<400> SEQUENCE: 22
ggagctggtg gcgtaggcaa gagtgccttg acgat        35

<210> SEQ ID NO 23
<211> LENGTH: 25
<212> TYPE: DNA
<213> ORGANISM: A Homozygote

<400> SEQUENCE: 23
ttataaggcc tgctgaaaat gacta        25

<210> SEQ ID NO 24
<211> LENGTH: 23
<212> TYPE: DNA
<213> ORGANISM: A Homozygote

<400> SEQUENCE: 24
atcgtcaagg cactcttgcc tac        23

<210> SEQ ID NO 25
<211> LENGTH: 521
<212> TYPE: DNA
<213> ORGANISM: A Homozygote

<400> SEQUENCE: 25
gcagtaggaa aaatgctggc cctgatgacc tgtccttatt cagaatgaga gactgcgggg        60
ggggcctggg ggtagtgtca atgcccctcc agggctggag gggaagaggg gccccgagga       120
tgggcctggg ctcagcattc gagatcttga gattgatttt tttttaaatc atgcaacctt       180
tccttaggaa gacatttggt tttcatcatg attaagatga ttcctagatt tagcacaatg       240
gagagattcc atgccatctt tactatgtgg atggtggtat cagggaagag ggctcacaag       300
acacatttgt cccccgggcc caccacatca tcctcacgtg ttcggtactg agcagccact       360
acccctgatg agaacagtat gaagaaaggg ggctgttgga gtcccagaat tgctgacagc       420
agaggctttg ctgctgtgaa tcccacctgc caccagcctg cagcacaccc tagaggcgaa       480
agcagtggct catcctacct gttaggagca ggtagggctt g                          521

<210> SEQ ID NO 26
<211> LENGTH: 19
<212> TYPE: DNA
<213> ORGANISM: A Homozygote

<400> SEQUENCE: 26
gcagtaggaa aaatgctgg        19

<210> SEQ ID NO 27
<211> LENGTH: 20
<212> TYPE: DNA
<213> ORGANISM: A Homozygote

<400> SEQUENCE: 27

```
caagccctac ctgctcctaa                                                    20

<210> SEQ ID NO 28
<211> LENGTH: 19
<212> TYPE: DNA
<213> ORGANISM: A Homozygote

<400> SEQUENCE: 28
taagaaaggt tgcatgatt                                                     19

<210> SEQ ID NO 29
<211> LENGTH: 522
<212> TYPE: DNA
<213> ORGANISM: A Homozygote

<400> SEQUENCE: 29
aaagtggggc ctggctacct gggcagtgga ggcagccgca actccagctc cctggaccac        60
ccggatgagc gggccctcac catgggcgac ctcatctcat tgcctggca gatctcacag        120 gggatgcagt atctggccga gatgaaggtg ccaccactgc ccctgccacc cacaccctgg       180
cctgccactc cccaccatgc cacactctag cccaccatgc ccctgccatg gcatgccatg       240
ctatggctca ccacgcccct gccatgtcac accctgactc caccacgccc ctgccatgcc       300
acacccccgg cccaggtctc accaggccgc tacccgggcc acacaccacc cctctgctgg       360
tcacaccagg ctgagccagt gaccgctgct gctgccatgg cctgacgaac tcgtgctatt       420
tttcctacag ctcgttcatc gggacttggc agccagaaac atcctggtag ctgaggggcg       480
gaagatgaag atttcggatt tcggcttgtc ccgagatgtt ta                          522

<210> SEQ ID NO 30
<211> LENGTH: 553
<212> TYPE: DNA
<213> ORGANISM: A Homozygote
<220> FEATURE:
<221> NAME/KEY: n
<222> LOCATION: (359)..(359)
<223> OTHER INFORMATION: a or g or c or t/u
<221> NAME/KEY: n
<222> LOCATION: (465)..(465)
<223> OTHER INFORMATION: a or g or c or t/u

<400> SEQUENCE: 30
tccatacagc cctgttctcc ctctttctcc ctttccctac tgctcctgcc ctgtttcctg        60
ttctccctct ttctggaagc ctggctcagg ccccagcctg gagcttgtgt ctagctgagt       120
ccacgggctg agtggtcact ttccatcaga ggggccccgc gctagcggca ctccctgggc       180
ccacagggct actcagaggt ctctggtgtg acactgccat gtgtcctcac ccagttcggg       240
gctgggccca tttggggcag ggagctctag gaatggacag tgcatcctgg gtactagggt       300
accctgggta ccacagggca ccaggtgtgc tgtgacctca ggtgacccca gccccgccnt       360
gcatggcagg aacattgtca ccatttctca gataaagacc caggagacca gcctggtttg       420
ttggttttcc aaaccaccat gctgctcagg gcttcccag catgngtgtg tgggtgtgtg        480
cgagagggat agggaaccca aacaccggga gtgcgcagca ggcactgtgg tcggcaccag       540
tagagttgga ggc                                                         553

<210> SEQ ID NO 31
<211> LENGTH: 527
<212> TYPE: DNA
<213> ORGANISM: A Homozygote
```

<400> SEQUENCE: 31

| | | | | | |
|---|---|---|---|---|---|
| gggaagggaa | gcttgtagga | ttctggacca | cagctctgag | agacctgagc | acagtggccc | 60 |
| actgggctgg | gatcctgcaa | caggccatgc | ccagtcccac | gaggctcaga | gatgtcagcg | 120 |
| atgcagaaat | agctttggag | ttggagacag | agcacactgg | gcccagggta | cagggcaggg | 180 |
| tgcgatggct | gtggtgggct | gtccttctga | gacctggccc | tgcttggatc | atattggcct | 240 |
| gtctgctctt | cccaccaggt | accgcctgat | gctgcaatgc | tggaagcagg | agccggacaa | 300 |
| aaggccggtg | tttgcggaca | tcagcaaaga | cctggagaag | atgatggtta | agaggagagt | 360 |
| gagtgcctgg | gtccaattcc | cacaagctga | agtggcttg | gggagactcc | agcctcaccc | 420 |
| cagggcagta | gttttagccc | tcagagttcc | cagtgtgggg | ccacagtggg | attgtgcaaa | 480 |
| gagagagagt | catgctctcc | cctgcatgca | gacagcagat | tgaaccc | | 527 |

<210> SEQ ID NO 32
<211> LENGTH: 19
<212> TYPE: DNA
<213> ORGANISM: A Homozygote

<400> SEQUENCE: 32
aaagtggggc ctggctacc                                              19

<210> SEQ ID NO 33
<211> LENGTH: 20
<212> TYPE: DNA
<213> ORGANISM: A Homozygote

<400> SEQUENCE: 33
taaacatctc gggacaagcc                                             20

<210> SEQ ID NO 34
<211> LENGTH: 20
<212> TYPE: DNA
<213> ORGANISM: A Homozygote

<400> SEQUENCE: 34
tccatacagc cctgttctcc                                             20

<210> SEQ ID NO 35
<211> LENGTH: 20
<212> TYPE: DNA
<213> ORGANISM: A Homozygote

<400> SEQUENCE: 35
gcctccaact ctactggtgc                                             20

<210> SEQ ID NO 36
<211> LENGTH: 20
<212> TYPE: DNA
<213> ORGANISM: A Homozygote

<400> SEQUENCE: 36
gggaagggaa gcttgtagga                                             20

<210> SEQ ID NO 37
<211> LENGTH: 20
<212> TYPE: DNA
<213> ORGANISM: A Homozygote

<400> SEQUENCE: 37

-continued gggttcaatc tgctgtctgc                                         20

<210> SEQ ID NO 38
<211> LENGTH: 14
<212> TYPE: DNA
<213> ORGANISM: A Homozygote

<400> SEQUENCE: 38
agactccctg ccca                                               14

<210> SEQ ID NO 39
<211> LENGTH: 9
<212> TYPE: DNA
<213> ORGANISM: A Homozygote

<400> SEQUENCE: 39 tttcacacc                                                     9

<210> SEQ ID NO 40
<211> LENGTH: 11
<212> TYPE: DNA
<213> ORGANISM: A Homozygote

<400> SEQUENCE: 40
ctgacccacc a                                                  11

<210> SEQ ID NO 41
<211> LENGTH: 9
<212> TYPE: DNA
<213> ORGANISM: A Homozygote

<400> SEQUENCE: 41 ctgtaggaa                                                     9

<210> SEQ ID NO 42
<211> LENGTH: 14
<212> TYPE: DNA
<213> ORGANISM: A Homozygote

<400> SEQUENCE: 42
aaaatagcac gagt                                               14

<210> SEQ ID NO 43
<211> LENGTH: 12
<212> TYPE: DNA
<213> ORGANISM: A Homozygote

<400> SEQUENCE: 43
tttttttttt ct                                                 12

<210> SEQ ID NO 44
<211> LENGTH: 15
<212> TYPE: DNA
<213> ORGANISM: A Homozygote

<400> SEQUENCE: 44
gagcacagtg gccca                                              15

<210> SEQ ID NO 45
<211> LENGTH: 22
<212> TYPE: DNA
<213> ORGANISM: A Homozygote

<400> SEQUENCE: 45

```
agtgcttaac aagaccatac ta                                            22

<210> SEQ ID NO 46
<211> LENGTH: 24
<212> TYPE: DNA
<213> ORGANISM: A Homozygote

<400> SEQUENCE: 46
tggaaagtct ttaagactct taaa                                          24

<210> SEQ ID NO 47
<211> LENGTH: 23
<212> TYPE: DNA
<213> ORGANISM: A Homozygote

<400> SEQUENCE: 47
tcaaggcact cttgcctacg cca                                           23
```

METHOD FOR GENOTYPING OF SINGLE NUCLEOTIDE POLYMORPHISM

This research was supported in part by NIH Grants No. HG01437 and HG01815.

BACKGROUND OF THE INVENTION

The most common polymorphisms in the human genome are single point mutations or single nucleotide polymorphisms also referred to as "SNPs". An single nucleotide polymorphisms is a change, such as a deletion, insertion or substitution, in any single nucleotide base in the region of the genome of interest. Genotyping of single nucleotide polymorphisms will make possible genome-wide association studies, which are a powerful methods for identifying genes that make a contribution to disease risk.

For example, a point mutation $G^{1691} \to A$ in the coagulation factor V gene, results in a $Arg^{506} \to Gln$ amino acid mutation in the factor V molecule. This mutation, defined as factor $V^{LEIDEN}$, leads to activated protein C (APC)-resistance and is the most common genetic risk factor for hereditary venous thrombosis.

Genotyping of single point mutations can be performed using a variety of assays, for example, a plasma based assay, Taqman, restriction digestion of PCR products, calorimetric mini-sequencing assay, radioactive labeled based solid-phase mini sequencing technique, allele-specific oligonucleotide (ASO), and single strand conformation polymorphism (SSCP). However, these methods are extremely time consuming.

Matrix-assisted laser-desorption/ionization time-of-flight (MALDI-TOF) mass spectrometry has been employed to genotype single nucleotide polymorphism, in two assays, the Pinpoint assay and the Probe assay. In the PINPOINT assay a primer is annealed to the target DNA immediately upstream of the single nucleotide polymorphism site. The primer is extended in the presence of all four ddNTPs, but not dNTP. As a result, the primer is extended by a single base. The base at the single nucleotide polymorphism site is identified by the mass added onto the primer. However, this method suffers from poor resolution, as the mass difference between difference between the ddNTP nucleotides is quite small. For example, the mass difference between ddT and ddA nucleotides can be as little as 9 Da, rendering it difficult to identify the added nucleotide. Also, the presence of salt adducts of Na, Mg and K from the buffers employed in the assay renders it difficult to accurately measure the mass peak positions. Removing the salt adducts requires extensive time consuming desalting procedures.

Attempts have been made to address the resolution problems by using mass-tagged dideoxynucleotides in place of the unmodified dideoxynucleotides. However, the presence of such mass tags slows sequencing reactions.

Another attempt was made to overcome the resolution problem by adding a cleavable site to the primer that can be cleaved after extension to produce lower mass markers that can be identified in a more accurate manner. However, this still required extensive de-salting and added an additional step of cleaving the primer.

PROBE is a method in which the primer is extended in the presence of three deoxy nucleotides (dNTPs) and a one dideoxynucleotide which is complementary to the nucleotides of one of the alleles. In this way, the primer is extended by one base by the addition of the ddNTP from one allele. Primers annealed to target DNA containing the other allele are extended by the addition of dNTPs until the ddNTP is eventually incorporated and the primer is terminated. The number of dNTPs added depends on the nucleotide sequence of the target DNA. However, the probe assay suffers from low detection sensitivity and peak overlapping because of the long extension products.

It would be desirable to have an assay for determining single nucleotide polymorphisms which has high resolution, high detection sensitivity, does not suffer from long extensions, and does not require extensive desalting.

SUMMARY OF THE INVENTION

A new assay for genotyping of single nucleotide polymorphisms has been developed, which has the advantage of high resolution, high detection sensitivity, no need for labeling, and does not require extensive desalting steps. Such new method, hereinafter referred to as the "VSET assay", tends to produce very short extension products. The VSET assay is accurate, fast, efficient and allows for simultaneous multiplex genotyping of a number of mutation sites. The VSET is also compatible with automation.

The VSET method of genotyping a nucleotide polymorphism comprises the following steps: providing a polynucleotide acid sample comprising at least one target site, and a first region of nucleotides immediately adjacent to the target site; preferably genomic DNA; preferably amplifying the polynucleotide; then combining the polynucleotide sample with: three dideoxynucletides selected from the group of ddGTP, ddATP, ddCTP, and ddTTP; and one deoxynucleotide selected from the group consisting of dGTP, dATP, dCTP, and dTTP wherein the nucleotide of the deoxynucleotide is not the same as the nucleotide in the dideoxynulceotide; and a mini-sequencing primer complementary to the first region of nucleotides; extending the mini-sequencing primer with a dideoxynucletide or deoxynulceotide whose base is complementary to the base at the target site, to provide extension products; and then identifying the extension products. It is highly preferred that the extension products be identified by mass spectrometry, preferably Matrix-assisted laser-desorption/ionization time-of-flight (MALDI-TOF) mass spectrometry.

In the VSET assay, mini-sequencing is conducted in the presence of: a nucleic acid polymerase, where the sample is DNA, then the polymerase is DNA polymerase; three dideoxy nucleotides; and one deoxynucleotide. One of the three ddNTPs is complementary to one of the allelic variations at the single point mutation site while the deoxynucleotide is complementary to the other allelic variant at the single point mutation site. The mini-sequencing primer hybridizes to a polynucleotide sequence immediately next to a single point mutation site and is extended by the polymerases. Typically, the extension products will contain either one or two nucleotides in addition to the primer sequence used in the mini-sequencing step. The genotype at the variable site is determined on the basis of the number of nucleotides contained in the extension products. This assay is particularly useful to genotype the factor V mutation in the Factor V gene, specifically the $G^{1691} \to A$ mutation of Factor V.

In the preferred form of the method to genotype the factor V mutation in the Factor V gene, a fragment of genomic DNA containing the $1691^{th}$ base is preferably first amplified, using conventional techniques, preferably conventional polymerase chain reaction techniques also referred to herein as "PCR". Next, mini-sequencing of the amplified polynucleotide is conducted in the presence of primers complementary to the nucleotides adjacent to the nucleotide polymorphism, and dGTP, ddATP, ddCTP, and ddTTP, to provide extension products. The extension products are analyzed preferably using mass spectrometry, preferably matrix-assisted-laser-desorption-ionization time-of-flight (MALDI-TOF) mass spectrometry. The base at position 1691 is identified based on the number of nucleotides added to the primer used in the mini-sequencing. Alternatively, to genotype the factor V mutation in the Factor V gene, mini-sequencing is conducted in the presence of dCTP and ddATP, ddGTP, and ddTTP.

VSET is also useful for multiplex genotyping, that is the genotyping of multiple single nucleotide polymorphisms. The multiple single nucleotide polymorphism sites may be distributed along one polynucleotides or may be distributed among more than one polynucleotides.

BRIEF DESCRIPTION OF THE FIGURES

FIG. 3A MALDI-TOF mass spectra of the extension products of Example 3a.

FIG. 3B MALDI-TOF mass spectra of the extension products of Comparative Example A.

FIG. 3C MALDI-TOF mass spectra of the extension products of Comparative Example B.

DETAILED DESCRIPTION OF THE INVENTION

Figure 1A:
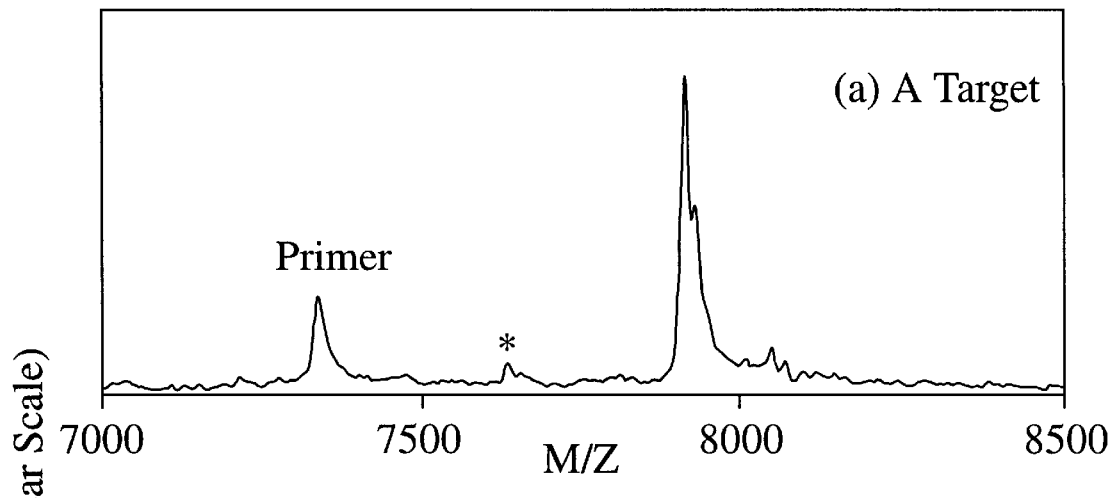
FIG. 1A MALDI-TOF mass spectra of the extension products of Example 1a which contain A at target site. The minor peak labeled with an asterisk was due to unterminated products.

The "VSET assay" tends to produce very short extension products. The VSET assay is accurate, fast, efficient and allows for simultaneous multiplex genotyping of a number of mutation sites. The VSET method determines the nucleotide base at a particular target site on a polynucleotide. Thus the VSET assay is particularly useful for genotyping a nucleotide polymorphism, particularly single nucleotide polymorphisms. Thus the method for determining a nucleotide at a target site on a polynucleotide comprises the following steps: providing a polynucleotide sample containing a nucleotide polymorphism site; amplifying the polynucleotide sample; then combining the amplified polynucleotide sample with: a nucleic acid polymerase, three dideoxynucletides selected from the group of ddGTP, ddATP, ddCTP, and ddTTP; and one deoxynucleotide selected to from the group consisting of and dGTP, dATP, dCTP, and dTTP wherein the nucleotide of the deoxynucleotide is not the same as the nucleotide in the dideoxynulceotide; and a primer complementary to the nucleotides adjacent to the nucleotide polymorphism to provide extension products; and then identifying the extension products. It is highly preferred that the extension products be identified by mass spectrometry, preferably Matrix-assisted laser-desorption/ionization time-of-flight (MALDI-TOF) mass spectrometry.

In the VSET assay, mini-sequencing is conducted in the presence of three dideoxy nucleotides, and one deoxynucleotide. One of the three ddNTPs is complementary to one of the allelic variations at the single point mutation site while the deoxynucleotide is complementary to the other allelic variant at the single point mutation site. The mini-sequencing primer hybridizes to a polynucleotide sequence immediately next to a single point mutation site and is extended by the DNA polymerases. Typically, the extension products will contain either one or two nucleotides in addition to the primer sequence used in the mini-sequencing step. The genotype at the variable site is determined on the basis of the number of nucleotides contained in the extension products.

A biallelic single nucleotide polymorphism yields three different genotypes. For example, an A/G marker could produce the genotype of A homozygote, G homozygote and A/G heterozygote. Table 1 illustrates the VSET method for genotyping of a single nucleotide polymorphism in (A/G) marker. The primer is annealed to the target DNA immediately upstream of the single nucleotide polymorphism site and is extended in the presence three ddNTPs, preferably (ddATP, ddGTP and ddCTP) and the fourth nucleotide in the deoxy form preferably dTTP.

TABLE 1

Mini-sequencing reaction of the VSET assay for gentotyping a model single nucleotide polymorphism A/G system.

(a) A Homozygote     Seq. ID. 1
3' ---TAGCAGTTCCGTGAGAACGGATGCGGTAGTC-----5' (template)
(Mini seq. primer) 5' TCAAGGCACTCTTGCCTACGCCA     Seq. ID. 2
↓ dTTP
↓ ddGTP, ddATP, ddCTP

TABLE 1-continued

Mini-sequencing reaction of the VSET assay for gentotyping a model single nucleotide polymorphism A/G system.

| | | |
|---|---|---|
| Two base Extension products | 5'TCAAGGCACTCTTGCCTACGCCAdTddC | Seq. ID. 3 |
| (b) G Homozygote | Seq. ID. 4 | |
| | 3' ---TAGCAGTTCCGTGAGAACGGATGCGGTGGTC-----5' (template) | |
| (Mini seq. primer) | 5'TCAAGGCACTCTTGCCTACGCCA | Seq. ID. 2 |
| | ↓ dTTP | |
| | ↓ ddGTP, ddATP, ddCTP | |
| (One Base Extension Products) | 5'TCAAGGCACTCTTGCCTACGCCAddC | Seq. ID. 5 |
| (c) A/G Heterozygote | | Seq. ID. 4 |
| 3' | ---TAGCAGTTCCGTGAGAACGGATGCGGTG/AGTC----5' | |
| (template) | | |
| (Mini seq. primer) | 5'TCAAGGCACTCTTGCCTACGCCA | Seq. ID. 2 |
| | ↓ dTTP | |
| | ↓ ddGTP, ddATP, ddCTP | |
| | | Seq. ID. 5 |
| One Base Extension Products | 5'TCAAGGCACTCTTGCCTACGCCAddC | |
| | | Seq. ID. 3 |
| Two Base Extension Products | 5'TCAAGGCACTCTTGCCTACGCCAdTddC | |

As shown in Table 1, using such nucleotides, the A homozygous sample produces two-base extension products, while the G homozygous sample yields one-base extension products. The A/G heterozygous sample gives both one- and two-base extension products. The genotype of the single point mutation site is identified on the basis of the primer extension pattern.

The primers are typically extended by either one or two bases in VSET. If the template sequence contains a run of the nucleotide that is the same as the base in the single nucleotide polymorphism site, and it immediately follows the single nucleotide polymorphism site, the primer may be extended by more than two bases. In this case, several measures can be taken. First, the combination of ddNTPs and dNTP should be altered and this change will limit extension to either one or two bases. Second, a new primer can be designed to target another strand. Third, the same reaction conditions are utilized and the primer is allowed to extend by three or four bases as long as the extension products will not lead to the overlapping problem.

The VSET assay is particularly useful to genotype the mutation in the Factor V gene, specifically the $G^{1691} \rightarrow A$ mutation of Factor V. In the preferred form of the method to genotype the mutation in the Factor V gene, a fragment of genomic DNA containing the $1691^{th}$ base is first amplified, using conventional techniques, preferably conventional polymerase chain reaction techniques also referred to herein as "PCR". Next, mini-sequencing of the amplified polynucleotide is conducted in the presence of primers complementary to the nucleotides adjacent to the nucleotide polymorphism, and dGTP, ddATP, ddCTP, and ddTTP, to provide extension products. The extension products are analyzed preferably using mass spectrometry preferably matrix-assisted-laser-desorption-ionization time-of-flight (MALDI-TOF) mass spectrometry. The base at position 1691 is identified based on the number of nucleotides added to the primer used in the mini-sequencing. Alternatively, to genotype the mutation in the Factor V gene, mini-sequencing is conducted in the presence of dCTP and ddATP, ddGTP, and ddTTP.

Table 2 presents a schematic overview of genotyping of the $1691^{th}$ base of the Factor V using the VSET method, and the bold letter labeled indicates the base of the $1691^{th}$ position. Since the antisense strand serves as the mini-sequencing templates, the base at this mutation site is either C (corresponding to G) or T (corresponding to A). There are three genotypes resulting from this mutation, which are G homozygote, A homozygote, and A/G heterozygote, respectively. As shown in Table 2, the G homozygous individual only generates two-base extension products (dG+ddA), whereas the A homozygous individual produces one-base extension products (ddA). In contrast, the A/G heterozygous individual yields both one- and two-base extension products.

TABLE 2

Mini-sequencing reaction of the VSET assay used to genotype the G 1691 –>A Mutation af the Factor V Gene.

(a) G Homozygote

3'ACATTCTCGTCTAGGGACCTGTCCGCTCCTTA 5' (Template)

(Mini Sequencing Primer)        5'GCAGATCCCTGGACAGGC

|dGTP
                                                            |ddATP, ddTTP, and ddCTP
                                                            ↓

GCAGATCCCTGGACAGGCdGddA

Results:ASingleTwo-BaseExtensionProduct (b) A Homozygote

3'ACATTCTCGTCTAGGGACCTGTCCGTTCCTTA 5' (Template)

TABLE 2-continued

Mini-sequencing reaction of the VSET assay used to genotype
the G 1691 −>A Mutation af the Factor V Gene.

(Mini Sequencing Primer)         5'GCAGATCCCTGGACAGGC
                                                    |dGTP
                                                    |ddATP, ddTTP, and ddCTP
                                                    ↓

GCAGATCCCTGGACAGGCddA
Results:ASingleOne-BaseExtensionProduct
(c) A/G Heterozygote
                        3'ACATTCTCGTCTAGGGACCTGTCCGTTCCTTA 5' (Template)
                                           C
(Mini Sequencing Primer)         5'GCAGATCCCTGGACAGGC
                                                    |dGTP
                                                    |ddATP, ddTTP, and ddCTP
                                                    ↓

GCAGATCCCTGGACAGGCddA
                                 GCAGATCCCTGGACAGGCdGddA
Results:BothOnBaseandTwo-BaseExtensionProducts

---

In addition to the $G^{1691} \to A$ mutation, other genetic polymorphisms are known in Factor V, for example $G^{20210} \to A$, and $A^{4070} \to G$. This VSET method allows simultaneous identification of the genotype of an individual in all these variation sites using a single tube reaction.

The Polynucleotide

The polynucleotide comprises at least one target site, preferably a single nucleotide polymorphism, and a first region of nucleotides immediately adjacent to the target site. The first region of nucleotides contains at least 5 nucleotides, preferably at least 7 nucleotides, more preferably at least 12 nucleotides more preferably at least 15 nucleotides. the first region serves as the site for hybridization of the mini-sequencing primers. As used herein "polynucleotide" embraces nucleic acids, for example, DNA, RNA, fragments of DNA or RNA, as well as oligonucleotides. The polynucleotide may be synthetic or genomic. The polynucleotide may be sense or anti-sense. A "polynucleotide sample" contains one or more polynucleotides.

When genotyping an individual, the polynucleotide is obtained preferably by extracting genomic DNA from blood or tissue samples.

While the invention has been described as particularly useful for assaying a single nucleotide polymorphism site, it is generally useful to identify one or more nucleotides in a polynucleotide.

The PCR Amplification

Amplification of the polynucleotide containing the single nucleotide polymorphism is performed where the sample amount is small. Thus while not essential it is highly preferred, particularly where the polynucleotide is genomic DNA. The amplification of the polynucleotide sample is by conventional techniques, to provide amplified polynucleotide sample. Preferably the amplification is by Polymerase Chain Reaction, hereinafter "PCR". The amplification primers are preferably from 16 to 45, more preferably from 20 to 25 nucleotides long.

The amplified products are preferably treated to remove residual dNTPs and unreacted primers, using conventional techniques. Preferably phosphatase and/or exonuclease, more preferably alkaline phosphatase and exonuclease I, are used to remove residual dNTPs and unreacted primers.

Mini-Sequencing

Next, the amplified polynucleotide sample is mini-sequenced to provide extension products. The minisequencing is a form of short chain extension in the presence of three ddNTPs and one deoxy nucleotide dNTP and a minisequencing primer. The minisequencing primer is complementary to some, or preferably all, of the nucleotides in the first nucleotide region of the target polynucleotide. The first nucleotide region is immediately adjacent to the nucleotide polymorphism site. Preferably the mini-sequencing primers are designed to hybridize with the nucleotide right next to the polymorphism site; however the mini-sequencing primers can hybridize several nucleotides away from the single polymorphism site. The mini-sequencing primers are preferably at least 5 nucleotides, more preferably at least 7 nucleotides, even more preferably at least 12 nucleotides long. Preferably the mini-sequencing primers are from 12 to 45, more preferably from 15 to 27 nucleotides long. The mini-sequencing is also conducted in the presence of a nucleic acid polymerase; where the sample is DNA, the polymerase is a DNA polymerase.

The mini-sequencing primer will be extended by either one or two bases depending upon the allelic variant contained in the sample DNA to which the primer has annealed. Specifically, the mini-sequencing primer is extended by one of the ddNTPs complementary to one allele, while it is normally extended by the addition of one dNTP, and then terminated by a ddNTP from another allele. As a result, the extension products which are the extended mini-sequencing primers, are preferably either one nucleotide base longer than the mini sequencing primer, or two nucleotide bases longer than the mini sequencing primer, or contain a mixture of both.

Desalting

Preferably, the extension products are desalted. While conventional desalting techniques can be employed in the VSET assay, it is a particular advantage that a simplified desalting procedure be used.

Analysis of the Extension Products

The extension products are then analyzed preferably using matrix-assisted-laser-desorption-ionization time-of-flight (MALDI-TOF) mass spectrometry. The nucleotide at the target site on the polynucleotide sample is identified based on the number of nucleotides added to the mini-sequencing primers. Thus when employed in genotyping, the genotype of the single nucleotide polymorphism site is identified based on the number of nucleotides added to the mini-sequencing primers.

Multiplex Genotyping

VSET is also useful for multiplex genotyping, that is the genotyping of multiple, preferably less than 50, single nucleotide polymorphisms. The multiple single nucleotide polymorphism sites may be distributed along one polynucleotide or may be distributed among more than one polynucleotide.

When multiplex genotyping is performed, the polynucleotide which contains the single nucleotide polymorphism site or sites may be amplified in a single tube. Alternatively, the polynucleotide are amplified separately, then the individual amplified polynucleotides are pooled.

However, in the multiplex assay, one allelic variant of the all polynucleotides targeted has the same nucleotide at the single nucleotide polymorphism sites. That is if for example five single nucleotide polymorphisims are genotyped their genotype is preferably a mix of g/a, g/c or g/t; rather than a mix of g/a, a/t, c/t, or c/a. In the mini-sequencing step the deoxynucleotide that is used is complementary to this nucleotide.

Each single nucleotide polymorphism site is targeted by its own primer; this primer is complementary to a sequence adjacent to its targeted single nucleotide polymorphism site. Each of the mini-sequencing primers hybridizes to a sequence immediately next to its targeted single nucleotide polymorphism site. In general, the extension products will contain either one or two nucleotides in addition to the mini-sequencing primers. The genotype of each single nucleotide polymorphism is determined on the basis of its targeting primer used and the number of nucleotides added to this primer.

Preferably the mini-sequencing primers are from 12 to 45, more preferably 15 to 27 nucleotide bases in length. Primers of such preferred lengths provide good extension efficiency and specificity. In addition, the peaks of doubly-charged or dimer ions of a given oligonucleotide would not overlap with the peaks of singly-charged monomer ions of other oligonucleotides, in order to provide good resolution.

Thus, 15–27 bases are preferred lengths for the primers of multiplex VSET assays. Because each primer and its extension products generally cover three bases, five different sets (15, 18, 21, 24 and 27 mers) of oligonucleotides are preferred as the primers. The primers of different sizes can be created with a 3' portion of the sequence complementary to the target and a 5' portion which is not complementary to the target. The 5' portion of the sequence serves as mass tag. Many primers can be created from each set of oligonucleotides as long as the masses of the unextended and extended primers are sufficiently different. For example, the average mass difference is ~50 Da, when six primers are created from each set of oligonucleotides. Therefore 30 primers (6×5) can be used to genotype 30 different single nucleotide polymorphism sites, by the VSET method in a single tube.

EXAMPLE 1a

The sample to be assayed was a synthetic oligonucleotide from Sigma Genosys (Woodlands, Tex.) and contained the variation site at the second base of codon 12 of the k-ras gene (GenBank ID: M54968). The second base of codon 12 contains the nucleotides A, C, G and T. Heterozygous samples were created by mixing equimolar amounts of two oligonucleotides that differed only at the second base of codon 12. The sequence of this oligonucleotide was:

Seq. ID. 11K- ras :ttata aggcctgctg aaaatgactg aatataaact tgtggtagtt ggagctggtg gcgtaggcaa gagtgccttg acgat The single nucleotide polymorphism site is indicated by the underlined/italicized nucleotide. The mini-sequencing of the DNA was performed in 20 µl which contained 1 µl of Target A (1 uM) synthetic DNA, 1 µl mini sequencing primer (5 uM), 2 µl of each ddNTPs and dNTP(ddATP, ddCTP, ddGTP and dTTP, all 0.3 mM, from Amersham Pharmaia Biotech), 2 µl of thermo sequenase reaction buffer (provided by the manufacturer which contained 260 mM Tris-HCl, pH 9.5, 65 mM $MgCl_2$), and 1 unit of thermo sequenase DNA polymerase, from Amersham Pharmaia Biotech, together with buffer. The mini-sequencing was performed with the following method, 94° C. for 2 minutes, 25 cycles at 94° C. for 20 seconds, 55° C. for 20 seconds using the thermal cycler(PCR-2400, PE Applied Biosystems, Foster City, Calif.). The mini-sequencing primer, which was purchased from Sigma Genosys, was:

5'-tcaaggcactcttgcctacgcca-3'. Seq. ID. 12

Thereafter, 2 µl of the ammonium acetate solution (10 M) was added to the mini-sequencing reaction tube, mixed with a vortex mixer. After incubating for about 10 minutes at room temperature, 80 µl of chilled pure ethanol were added, and gently mixed by inverting the tube several times. The tube was incubated in a freezer at −20° C. for about 30 minutes. Then the tube was centrifuged, at 13000×g for 15 minutes, the ethanol was decanted and, 100 µl of 70% chilled ethanol was added, and the tube was inverted several times to wash the DNA precipitation. The tube was centrifuged at 13000×g for 5 minutes and the supernatant was removed. The tube was drained on clean absorbent paper and the tube was heated at 65° C. for a few minutes to dry. Next, 5 µl of pure water was added to re-dissolve the precipitated DNA, to provide the purified, mini-sequencing extension products.

A matrix solution was prepared which contained saturated 3-hydropicolinic acid in a 1:1:2 mixture of water, acetonitrile and 0.1 M ammonium citrate.

Next, 0.5 µl of the matrix solution was applied to the MALDI plate which is stainless steel and allowed to air dry. Then 0.5 µl of the mini-sequencing extension products were added to the dried matrix and allowed to air dry. The sample was then analyzed using matrix-assisted-laser-desorption-ionization time-of-flight (MALDI-TOF) mass spectrometer, Dynamo, from Thermo Bioanalysis, Santa Fe, N.Mex. The negative ion mode was used to collect all spectra and all spectra were averaged over 10 shots. The results are shown in FIG. 1A.

EXAMPLE 1b

Figure 1B:
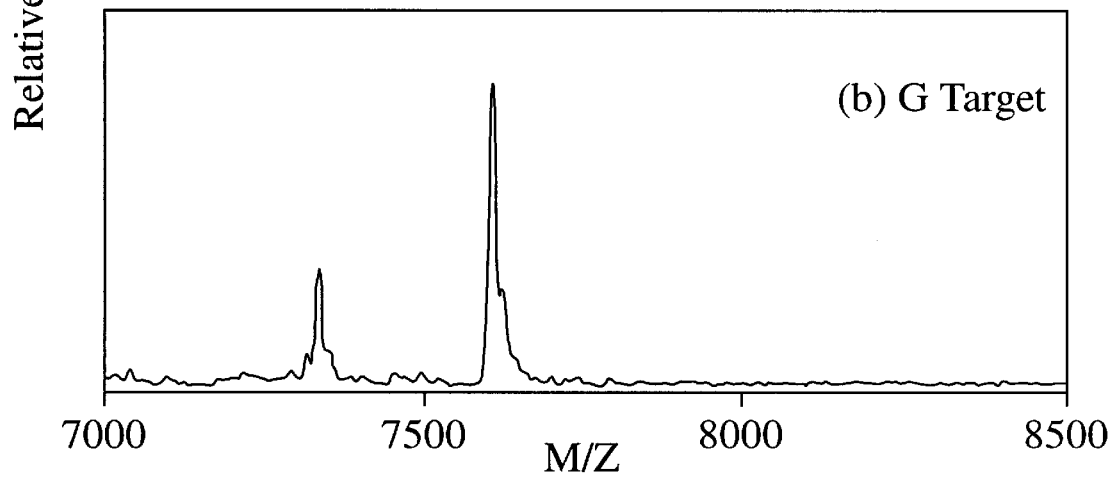
FIG. 1B MALDI-TOF mass spectra of the extension products Example 1b which contain G at target site.

1 µl of (1 µM) synthetic DNA as in Example 1a, except that the synthetic DNA contains a "G" at the target site, was analyzed as in Example 1a. The results are shown in FIG. 1B.

EXAMPLE 1c

Figure 1C:
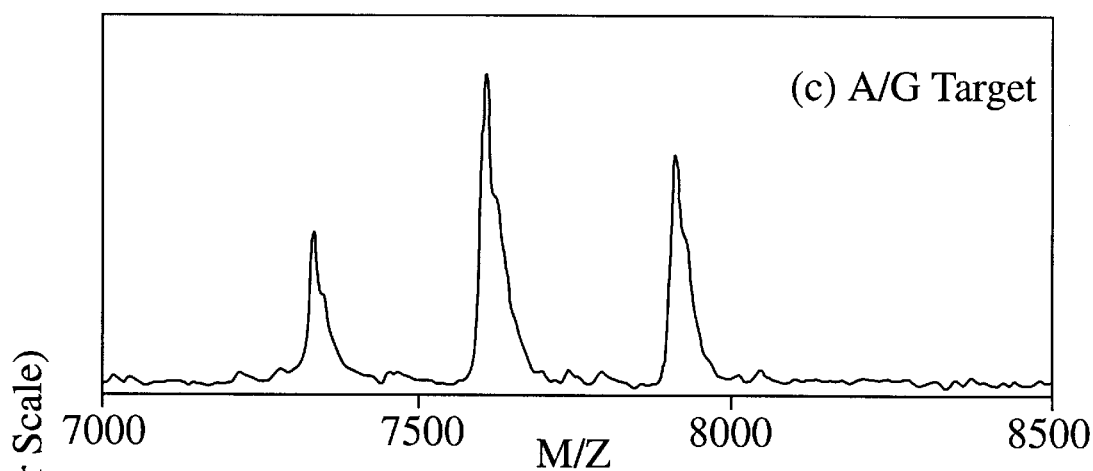
FIG. 1C MALDI-TOF mass spectra of the extension products of Example 1c which contain A/G at target site.

1 µl (1 µM) of a mixture of synthetic DNA as in Example 1a, except that the synthetic DNA contains either an A or a G at the target site was analyzed as in Example 1a. The results are shown in FIG. 1C.

EXAMPLE 1d

Figure 1D:
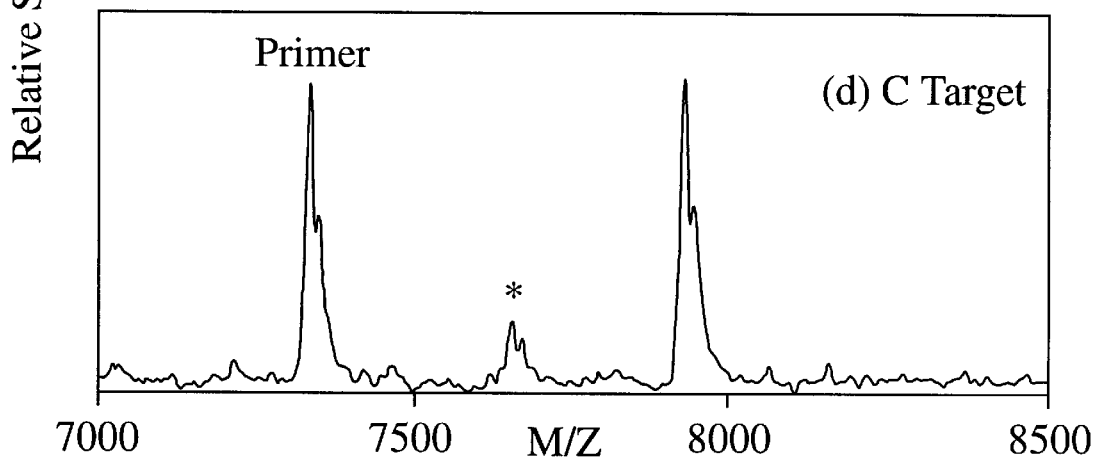
FIG. 1D MALDI-TOF mass spectra of the extension products of Example 1d which contain C at target site. The minor peak labeled with an asterisk was due to unterminated products.

1 µl of (1 µM) synthetic DNA as in Example 1a, except that the synthetic DNA contains a C at the target site except that the mini sequencing primer reaction was performed in the prescenceof 2 µl of each of ddATP, ddCTP, ddTTP, and dGTP (0.3 mM). The results are shown in FIG. 1D.

EXAMPLE 1e

Figure 1E:
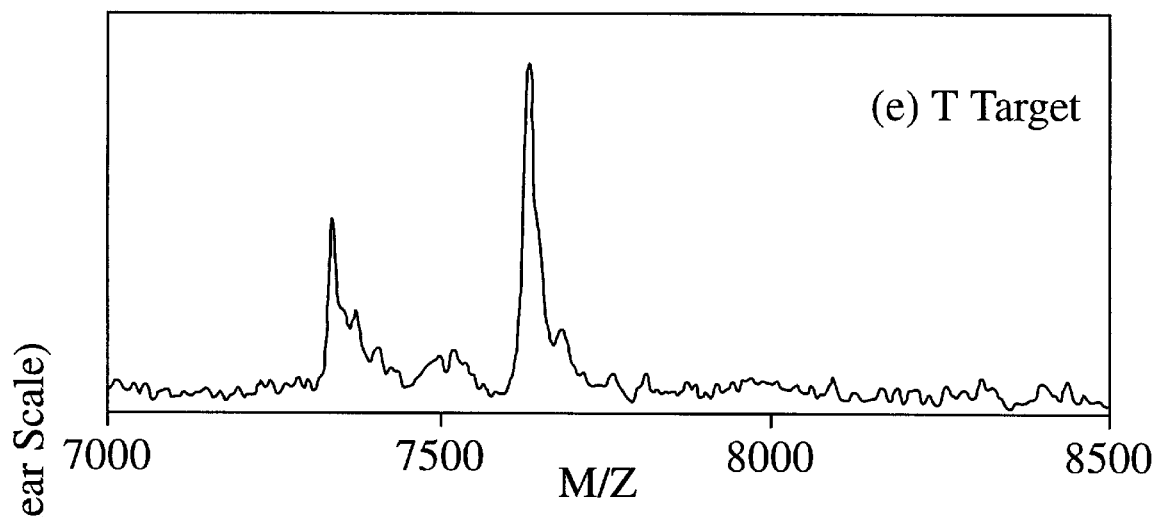
FIG. 1E MALDI-TOF mass spectra of the extension products of Example 1e which contain T at target site.

1 µl of (1 µM) synthetic DNA as in Example 1d, except that the synthetic DNA contains a T at the target site. The results are shown in FIG. 1E.

EXAMPLE 1f

1 μl (1 μM) of a mixture of synthetic DNA as in Example 1d, except that the synthetic DNA contains either an C or a T at the target site was analyzed as in Example 1d. The results are shown in FIG. 1F.

FIGS. 1A–C display the result of typing three different genotypes arising from A and G targets in the presence of ddATP, ddCTP, ddGTP and dTTP. As expected, the homozygous G target yields one-base extension product containing the additional ddC, while the homozygous A target generated two-base extension product containing the additional dT and ddC. The heterozygous A/G target produced both the one and two-base extension products.

Figure 1F:
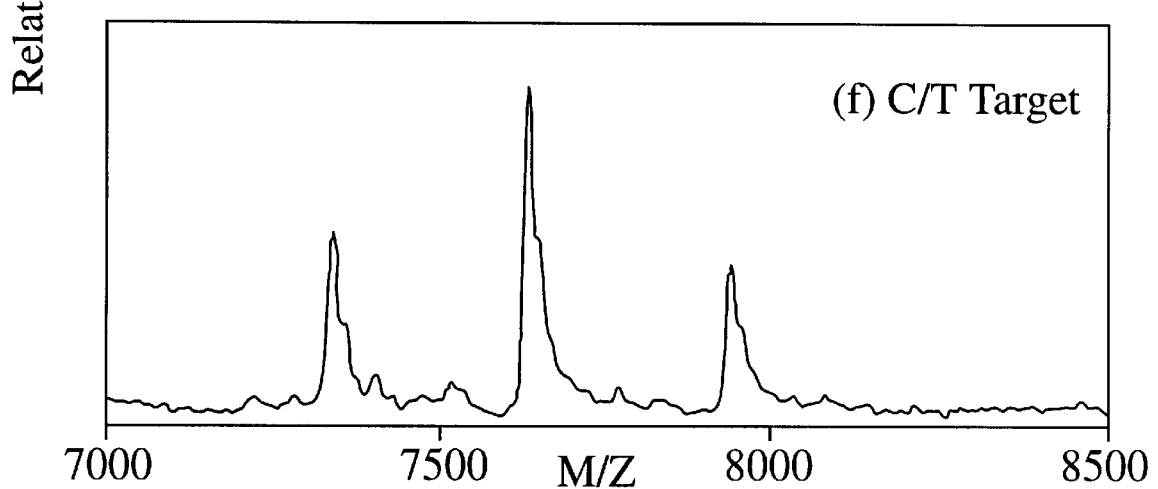
FIG. 1F MALDI-TOF mass spectra of the extension products of Example 1f which contain C/T at target site.

FIGS. 1D–F display the mass spectra of three different genotypes of the C and T target samples, in the presence of ddTTP, ddGTP, ddATP and dGTP. As expected, the homozygous T samples produced only one-base extension products by the addition of ddA, while the homozygous C sample yielded only two-base extension products by adding dG and ddC. In contrast, both one- and two-base extension products were produced where the heterozygous C/T target samples were used, as seen in FIG. 1F. Comparing the expected extension patterns with FIG. 1, it was seen that all six different targets were correctly identified.

As seen from FIGS. 1C and 1F, two extension products yielded from a heterozygote sample would have similar peak intensities and thereby, the genotype (homozygote or heterozygote) of a sample can be easily identified simply by comparing the peak intensity of products. For example, because the intensity of the peak labeled with an asterisk in FIG. 1A was significantly weaker than that of another extension products, it was concluded that the product corresponding to this minor peak was not terminated by a ddNTP and that the sample typed was homozygous.

EXAMPLE 2a

The sample and the single nucleotide polymorphism site to be assayed were the same synthetic polynucleotide as used in Example 1A. However, the single-strand synthetic DNA (either homozygous or heterozygous targets of A/T) were first amplified by PCR.

PCR was performed using a thermal cycler model PCR-2400, from PE Applied Biosystems, Foster City, Calif. The 25 μl mixture solutions were prepared with the buffer provided by the manufacturer. The primers used in PCR were:

Left primer: 5'-ttataaggcctgctgaaaatgacta-3' Seq. ID. 13
Right Primer: 5'-atcgtcaaggcactcttgcctac3' Seq. ID. 14

1 μl of Target A (1 pM), 1 μl of each PCR primers (10 μM), 2.5 μl of dNTPs (dATP, dCTP, dGTP, dTTP, each 2 mM), 2.5 μl of 10×PCR buffer, and 1 unit of Tag DNA polymerase, from Promega, were combined. The PCR buffer contained 50 mM KCl, 10 mM Tris-HCl, pH 9.0, at 25° C., 1.5 mM $MgCl_2$ and 0.1% Triton X-100 when diluted 1:10. PCR was conducted as follows: 94° C. for 2 minutes, 35 cycles at 94° C. for 30 seconds, 58° C. for 30 seconds, 72° C. for 30 seconds, finally heated at 72° C. for 5 minutes, and then stored at 4° C.

Thereafter, the PCR products were treated by alkaline phosphatase and exonuclease I to destroy residual dNTPs and PCR primers. Specifically, 1 unit of shrimp alkaline phosphatase (1 unit/μl) and 1 unit of exonuclease I (1 unit/μl), both from Amersham Pharmacia Biotech, Piscataway, N.J. were added to the PCR tube. Then, the tube was incubated at 37° C. for 30 minutes, followed by heating the tube at 80° C. for 15 minutes to deactivate the alkaline phosphatase and exonuclease I.

The amplified oligonucleotide was then mini-sequenced as in Example 1a, except that ddCTP, ddTTP, ddGTP and dATP were used in the mini-sequencing. The results are shown in FIG. 2A.

EXAMPLE 2b

1 μl (1 pM) of a synthetic DNA as in Example 2a, except that the synthetic DNA contained T at the target site was analyzed as in Example 2a. The results are shown in FIG. 2B.

EXAMPLE 2c

1 μl (1 pM) of a mixture of synthetic DNA as in Example 2a, except that the synthetic DNA contained either a T or an A at the target site was analyzed as in Example 2a. The results are shown in FIG. 2C.

Figure 2:
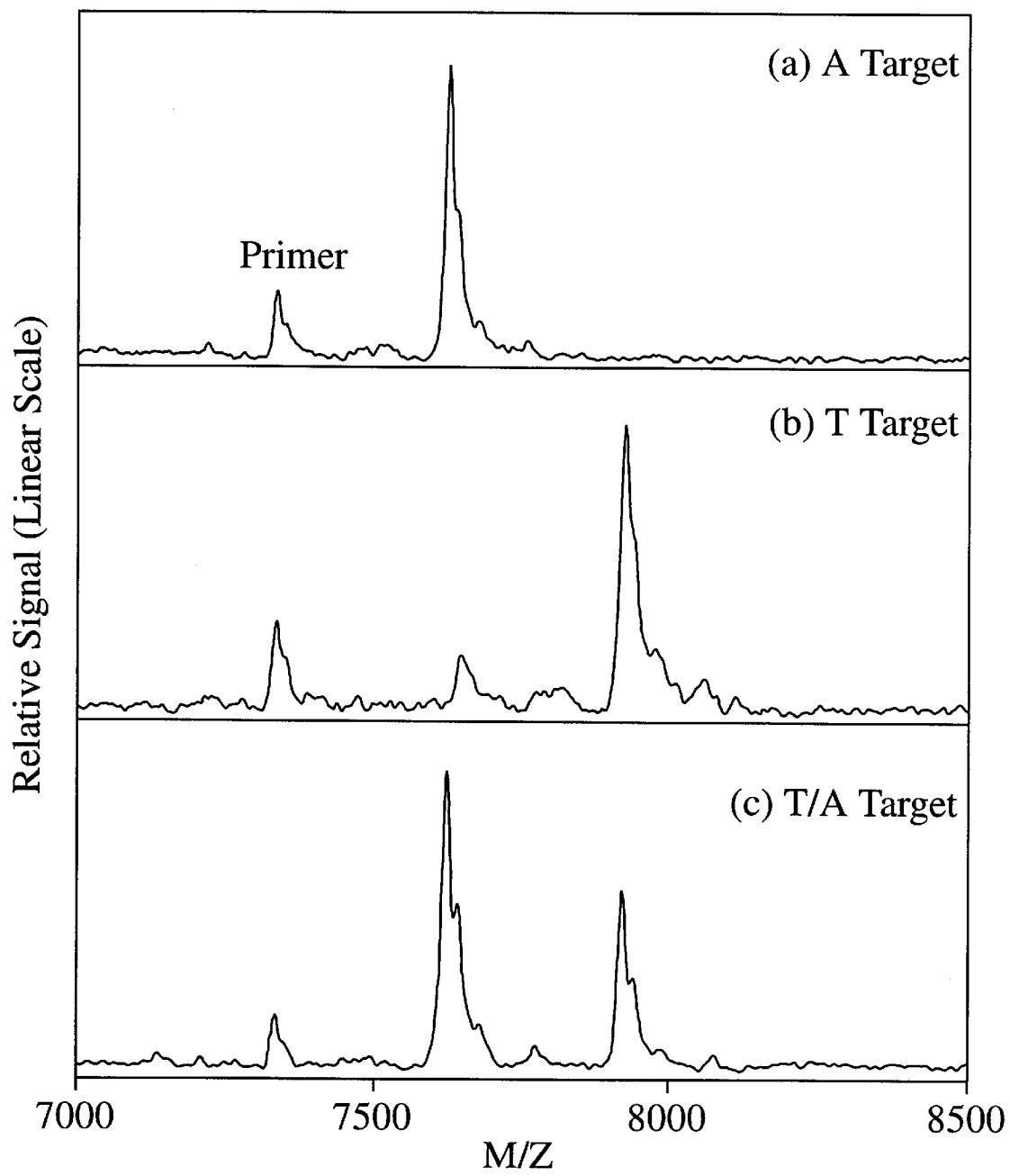
FIG. 2A MALDI-TOF mass spectra of the extension products of Example 2a which contain A at target site.
FIG. 2B MALDI-TOF mass spectra of the extension products of Example 2b which contain T at target site.
FIG. 2C MALDI-TOF mass spectra of the extension products of Example 2c which contain A/T at target site.

As a result, the DNA sample of Example 2a, which contain the A nucleotide at the polymorphism site, produced one-base extension products, while the DNA of Example 2b, which contained the T nucleotide target yielded two-base extension products. The A/T heterozygous DNA sample of Example 2c produced both one- and two-base extension products. FIG. 2 shows the spectra of the extension products from Examples 2a–c. As seen from FIG. 2, the primers were extended according to the genotype and three genotypes of A/T were unambiguously identified.

EXAMPLE 3

A 530 bp DNA fragment was used which contained the single nucleotide polymorphism site genbank (AJ243297/29366) and which has the sequence:

| | | | | | |
|---|---|---|---|---|---|
| gcagtagga agactgcggg | aaaatgctgg | ccctgatgac | ctgtacttat | tcagaatgag | Seq. ID. 15 |
| ggggcatgg ggccccgagg | gggtagtgtc | aatgccactc | cagggctgga | ggggaagagg | |
| atgggcctgg atgcaacctt | gctcagcatt | cgagatcttg | agaatgattt | tttttt/aaatc | |
| tccttaggaa tagcacaatg | gacatttggt | tttaataatg | attaagatga | ttcctagatt | |
| gagagattcc ggctcacaag | atgccatctt | tactatgtgg | atggtggtat | cagggaagag | |

```
acacatttgt   ccccggggcc   caccacatca   tcctcacgtg   ttcggtactg
agcagccact acccctgatg   agaacagtat   gaagaaaggg   ggctgttgga   gtcccagaat
tgctgacagc agaggctttg   ctgctgtgaa   tcccacctgc   caccagcctg   cagcacaccc
cacagccaag tagaggcgaa agcagtggct catcctacct gttaggagca ggtagggctt g
```

The bases labeled by the italicized letters is the single nucleotide polymorphism site; the alternative nucleotides are indicated. The DNA fragment was first amplified with PCR using the following primers:

Left primer: 5'-gcagtagga aaaatgctggc-3' Seq. ID. 16
Right Primer: 5'-caagccctacctgctcctaa-3' Seq. ID. 17

The amplified product was treated with alkaline phosphatase and exonuclease I as in Example 2a. The mini-sequencing was performed in the presence of ddATP, ddCTP, ddGTP and dTTP and utilized the mini-sequencing primer:

5'-taagaaaggttgcatgatt-3'. Seq. ID. 18

Mini sequencing reaction was performed in 20 μl with 5 μl of the amplified oligonucleotide. 1 μl of the mini sequencing primer (5 μM), 2 μl of Thermo sequenase buffer, 1 unit of Thermo sequenase DNA polymerase were used and the sample was minisequenced as in Example 1A.

EXAMPLE 4

A total of four other single nucleotide polymorphism sites were also examined and their ID/ single nucleotide polymorphism sites in GenBank were AJ243297/19274, AJ243297/20297, AJ243297/20547, and AJ243297/25187. For AJ243297/20297 and AJ243297/25187, the sense primers were designed to target the anti-sense strand templates, while for AJ/243297/19274 and AJ24397/20254, the anti-sense primers were designed to target the sense strand templates. Human genomic DNA samples, provided by Professor Chakravarti of Case Western Reserve University, were assayed The SNP 1,2 AJ243297/20297 and AJ243297/20547 sites have the following sequence:

```
aaagtggggc   ctggctacct   gggcagtgga   ggcagccgca   actccagctc   Seq. ID. 19 cctggaccac   ccggatgagc   gggccctcac   catgggcgac   ctcatctcat ttgcctggca   gatctcacag   gggatgcagt   atCtggccga   gatgaaggtg cgtgcatatg   gctctgcacc   cagccagccc   cggccaggcc   acaccctgac ccaccac/tgcc   cctgccaccc   acacccctggc   ctgccactcc   cccaccatgc cacactctag   ccaaccatgc   ccctgccatg   gcatgccatg   ctatggctca ccacgcccct   gccatgtcac   accctgactc   caccacgccc   ctgccatgcc acaccccgg   cccaggtctc   accaggccgc   tacccgggcc   acacaccacc cctctgctgg   tcacaccagg   ctgagccagt   gaccgctgct   gctgccatgg cctgacg/aact   cgtgctattt   ttcctacagc   tcgttcatcg   ggacttggca gccagaaaca   tcctggtagc   tgagggggcgg   aagatgaaga   tttcggattt cggcttgtcc cgagatgttt a
```

SNP 3/ AJ243297/19274 has the following sequence:

```
tccata cagccctgtt ctccctcttt ctcccttttcc ctactgctcc tgccctgttt   Seq. ID. 20 cctgttctcc   ctctttctgg   aagcctggct   caggcccccag   cctggagctt gtgtctagct   gagtccacgg   gctgagtggt   cactttccat   cagaggggcc ccgcgctagc   ggcactccct   gggcccacag   ggctactcag   aggtctctgg tgtgacactg   ccatgtgtcc tcacccagtt   cggggctggg   ccca/ttgggc agggagctct   aggaatggac   agtgcatcct   gggtactagg   gtaccctggg taccacaggg   caccaggtgt   gctgtgacct   caggtgaccc   cagccccgcc
```

-continued

```
ntgcatggca    ggaacattgt    caccatttct         cagataaaga    cccaggagac cagcctggtt         tgttggtttt ccaaaccacc         atgctgctca    ggggcttccc agcatgngtg    tgtgggtgtg         tgcgagaggg    atagggaacc    caaacaccgg gagtgcgcag caggcactgt ggtcggcacc    agtagagttg gaggc
```

SNP 5/ AJ243297/25187 has the following sequence:

```
        gggaa    gggaagcttg    taggattctg    gacaacagct    ctgagagacc tgagcacagt    ggccca c/t ggg    ctgygatcct    gcaacaggca    atgcccaagt cccacgaggc    tcagagatgt    cagcgatgca    gaaatagctt    tggagttgga gacagagcac    actgggccca    gggtacaggg    cagggtgcga    tggctgtggt gggctgtcct    tctgagacct    ggccctgctt    ggatcatatt    ggcctgtctg ctcttcccac    caggtaccgc    ctgatgctgc    aatgctggaa    gcaggagccg gacaaaaggc    cggtgtttgc    ggacatcagc    aaagacctgg    agaagatgat ggttaagagg    agagtgagtg    cctgggtcca    attcccacaa    gctgaaagtg gcttggggag    actccagcct    caccccaggg    cagtagtttt    agccctcaga gttcccagtg    tggggccaca    gtgggattgt    gcaaagagag    agagtcatgc tctcccctgc atgcagacag cagattgaac cc
```

The PCR amplification was first performed separately for each sample as in Example 3, except that different primers were used. For SNP 1,2(AJ243297/20297,20547) the PCR primers were:
Left primer: 5'-aaagtggggcctggctacc-3' Seq. ID. 22
Right Primer: 5'-taaacatctcgggacaagcc-3' Seq. ID. 23
For SNP 3/ (AJ243297/19274) the PCR primers were:
Left primer: 5'-tccata cagccctgtt ctcc-3' Seq. ID. 24
Right Primer: 5'-gcctccaactctactggtgc-3' Seq. ID. 25
For SNP 5/ (AJ243297/25187) the PCR primers were:
Left primer: 5'-gggaa gggaagcttg tagga-3' Seq. ID. 26
Right Primer: 5'-gggttcaatctgctgtctgc-3' Seq. ID 27
The samples were mini-sequenced according to Example 1a except that different mini-sequencing primers were used; the mini sequencing primers are those shown in Table 3. Also the ddNTPs and dNTPs differed, ddATP, ddCTP, ddGTP and dTTP were used.
VSET correctly identified the genotype of all the samples.

EXAMPLE 5

Multiplex Genotyping

Four single nucleotide polymorphism sites (AJ243297/19247, AJ243297/20297, AJ243297/20547 and AJ243297/25187) were examined. For AJ243297/20297 and AJ243297/25187, the sense primers were designed to target the anti-sense strand templates, while for AJ/243297/19274 and AJ24397/20254, the anti-sense primers were designed to target the sense strand templates. As a result, the targeted bases at all four single nucleotide polymorphism sites was G/A.

The PCR amplification was performed separately for each sample according to Example 4. Then the amplified polynucleotide samples were pooled together for mini-sequencing. The mini-sequencing was performed as in Example 1a except that it was performed in 30 µl, and 2.5 µl of each treated PCR product, 2.5 pmol of each mini sequencing primer, 3 µl of a combination of ddATP, ddCTP, ddGTP, and dTTP (each 0.3 mM), and 3 units of Thermo sequenase buffer were used. For desalting, 3 µl of 10 M ammonium acetate solution was used and 120 µl of cooled pure ethanol was used.

Figure 4:
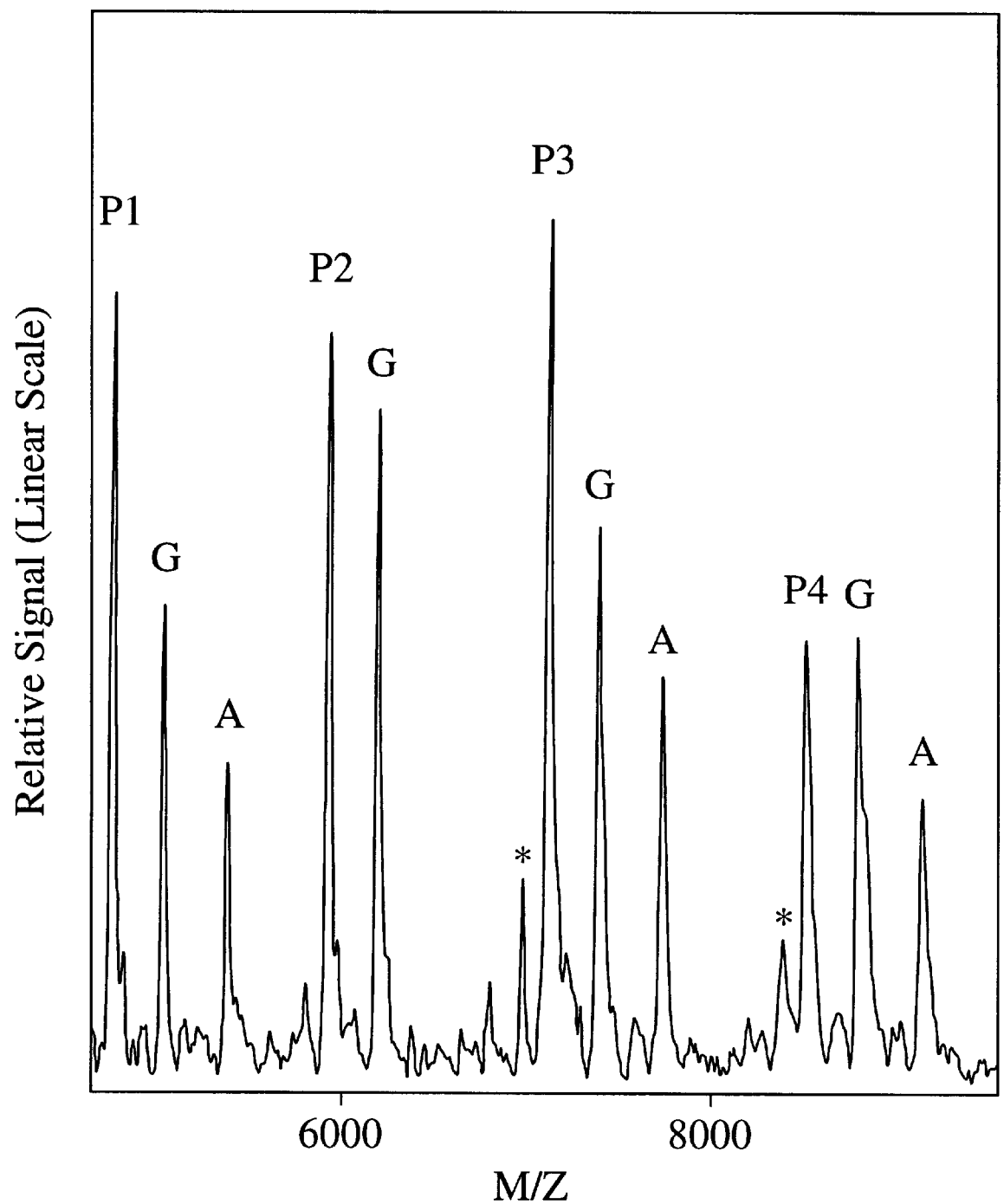
FIG. 4 MALDI-TOF mass spectra of the extension products of Example 5 which contained four different single nucleotide polymorphism sites in a single tube. Peaks labeled with an asterisk are due to impurities in primers.

The sequence of mini-sequencing primers and their expected extension products are listed in Table 3. The four mini-sequencing primers were either 15, 20, 24 or 27 bases in length. The portion of the primer sequence underlined in Table 3 acted as mass tags and the remaining sequences targeted the templates. FIG. 4 displays the result of the 4-fold multiplexed assay.

TABLE 3

Mini-sequencing primers and the expected extension products

| Primer | GenBank ID/SNP site | Mass of primer (Da) | Sequence (5' 3') | Seq. ID # | Genotype | Expected extension |
|---|---|---|---|---|---|---|
| P1 | AJ2342g7/19274 | 4772 | AGACTCCCTGCCCA | SEQ. ID 28 | A/G | A (dTddG)/ G (ddC) |

TABLE 3-continued

Mini-sequencing primers and the expected extension products

| Primer | GenBank ID/SNP site | Mass of primer (Da) | Sequence (5' 3') | Seq. ID # | Geno-type | Expected extension |
|---|---|---|---|---|---|---|
| P2 | AJ243297/20297 | 5923 | TTTCACACCCTGACCCACCA | SEQ. ID 29 | G | G (ddC) |
| P3 | AJ243297/20547 | 7124 | CTGTAGGAAAAAATAGCACGAGT | SEQ. ID 30 | A/G | A (dTddG)/ G (ddC) |
| P4 | AJ243297/25187 | 8500 | TTTTTTTTTTCTGAGCACAGTGGCCCA | SEQ. ID 31 | A/G | A (dTddG)/ G (ddC) |

The primers extended according to the expected extension pattern and therefore the genotypes of all four single nucleotide polymorphism sites were identified based on FIG. 4. The minor peaks labeled with an asterisk in FIG. 4 were due to impurities present in the primers provided by the manufacturers. Such impurities can be removed using conventional techniques such as HPLC and PAGE purification.

EXAMPLE 6

Blood samples were collected from 11 healthy and 16 patients who are APC-resistant as determined using conventional genotyping methods. Genomic DNA was extracted using GenomicPrep Blood DNA isolation kit from Amersham Pharmacia Biotech, Piscataway, N.J. according to the manufacturer's instructions. Then, the nucleic acids were resuspended with 100 μL deionized water, and 2 μL of the extracted DNA was used for the polymerase chain reaction. PCR primers were employed to amplify a 160 base fragment containing the $G^{1691} \rightarrow A$. The primers used in PCR were:

5'AGTGCTTAACAAGACCATACTA 3' (forward) Seq. ID. 35 and 3' TGGAAAGTCTTTAAGACTCTTAAA 5' (reverse). Seq. ID. 36

PCR was performed in a total volume of 20 μL containing a mixture of 10 units Taq DNA polymerase from Promega, Madison, Wis., 100×buffer, 2 μL of 0.2 mM of each dNTPs. The amplification reaction was carried out for 30 cycles of 30 seconds at 94° C., 30 seconds at 54° C., and 30 seconds at 72° C. in a thermocycler PCR-2400 PE Biosystems. Thereafter, PCR products were treated with 1 unit of Exonuclease I and Shrimp Phosphatase for 20 minutes and 10 minutes at 80° C. to destroy the unincorporated primers and nucleotides.

Next, 5 μL of the amplified polynucleotide sample were mixed with 5 pmol of the mini-sequencing primer, 1 unit Thermo Sequenase from Amersham Pharmacia Biotech, Piscataway, N.J., 2 μL of 10×ThermoSequenase buffer, 0.2 mM of dGTP, and 15 μM of ddNTPs (N=A, C, T, respectively) in a 20 μL final mixture. The antisense strand of the DNA was used as the target. The mini-sequencing primers were:

5' TCAAGGCACTCTTGCCTACGCCA 3' Seq. ID. 47

The extension reaction was performed for 40 cycles of 30 seconds at 94° C., 30 seconds at 56° C., and 30 seconds at 72° C., to provide extension products. The extension products were desalted using ethanol precipitation as in example 1a. Genotyping was performed in a blinded manner. The genotype of the 16 heterozygous and homozygous factor $V^{Leiden}$ individuals was not known to the operator before genotyping of all samples was completed. After genotyping, the mass spectrometric results were compared with the results obtained by conventional methods. Eleven normal individuals were tested as controls.

Figure 5:
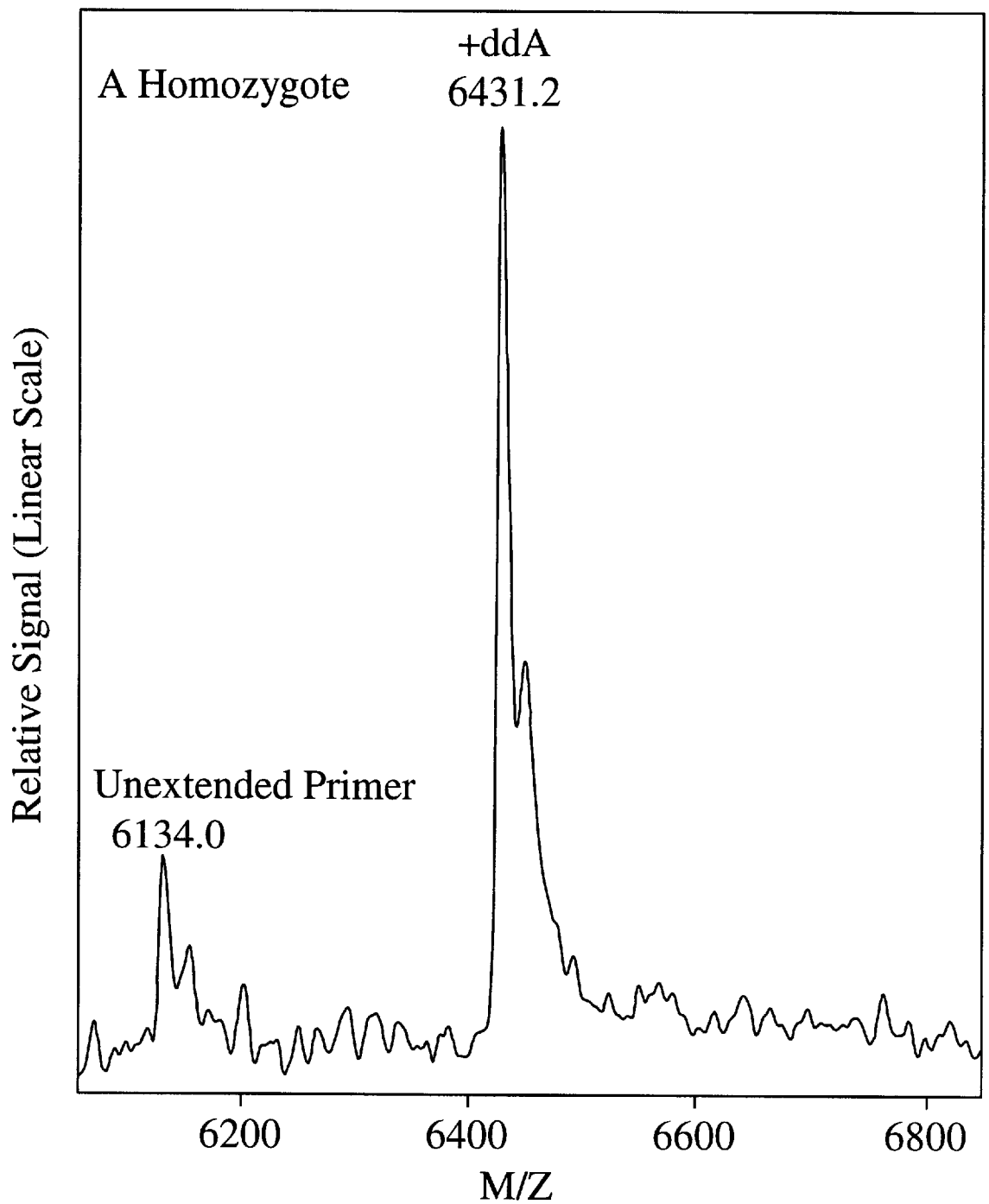
FIG. 5 MALDI-TOF mass spectrum of the extension products from an individual as described in Example 6, which were produced from an individual of A homozygote.

The genotypes of all 27 individuals were correctly identified by the VSET assay; the results correlated with the predicted results. Among 27 people, 12 individuals were identified as A/G heterozygote, 4 were A homozygote, and 11 were G homozygote. FIG. 5 shows a typical mass spectrum of the extension products obtained from Person 10. Only one extension product appeared in this mass spectrum, and this product was produced by the addition of one base (ddA). Comparing this spectrum with the expected extension pattern in Table 2, it was concluded that this individual has a genotype of A homozygote.

The spectra obtained from 3 other individuals, who were also identified as A homozygote, were similar to the spectrum shown in FIG. 5.

Figure 6:
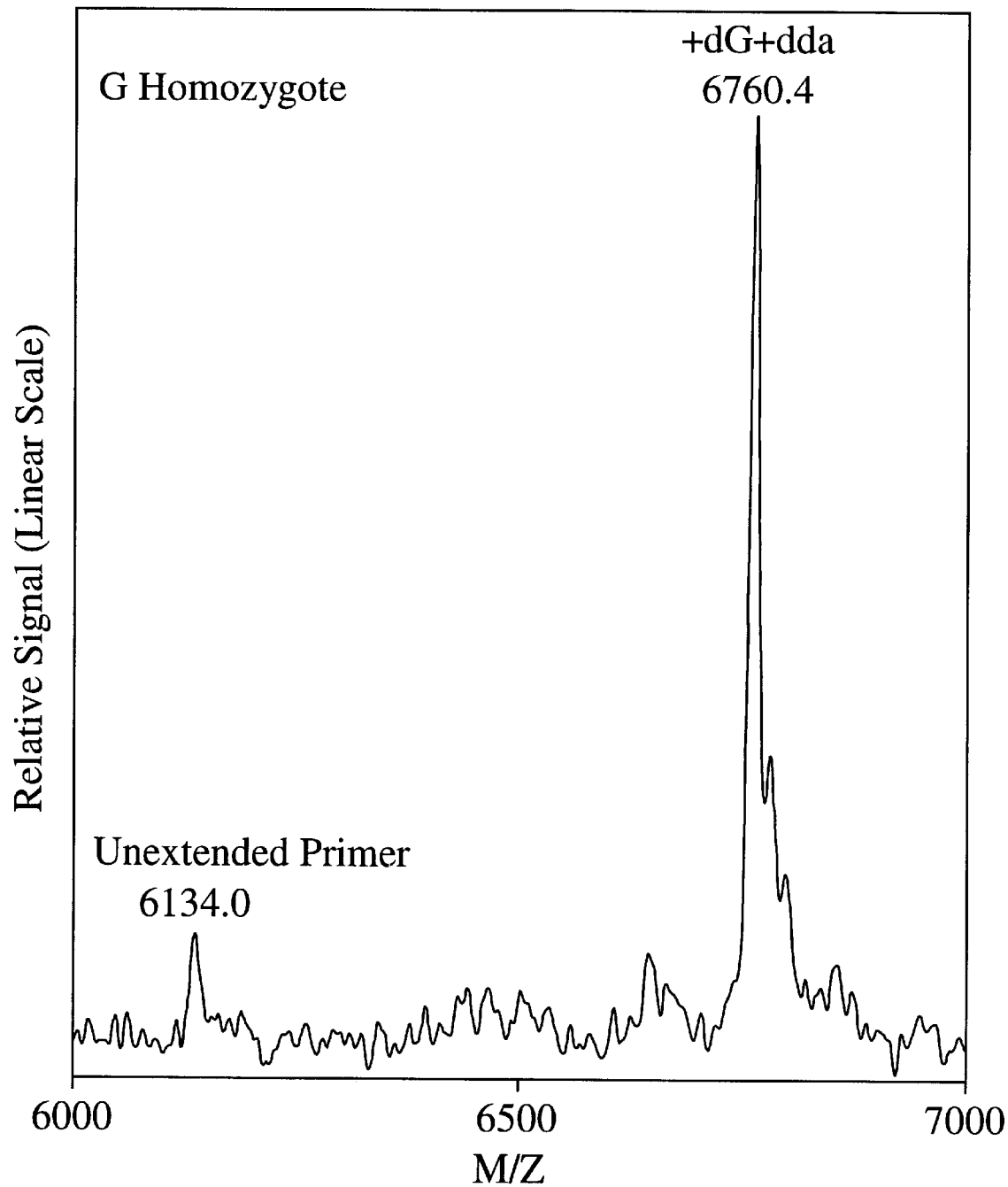
FIG. 6 MALDI-TOF mass spectrum of the extension products from an individual as described in Example 6, which were produced from an individual of G homozygote.

FIG. 6 shows the mass spectrum of the extension products obtained from Person 7. One product peak appeared in FIG. 6, and that was produced by the addition of two bases; thus this individual was G homozygote. The spectra obtained from 10 other individuals, who were also identified as G homozygote, were similar to the spectrum shown in FIG. 6.

Figure 7:
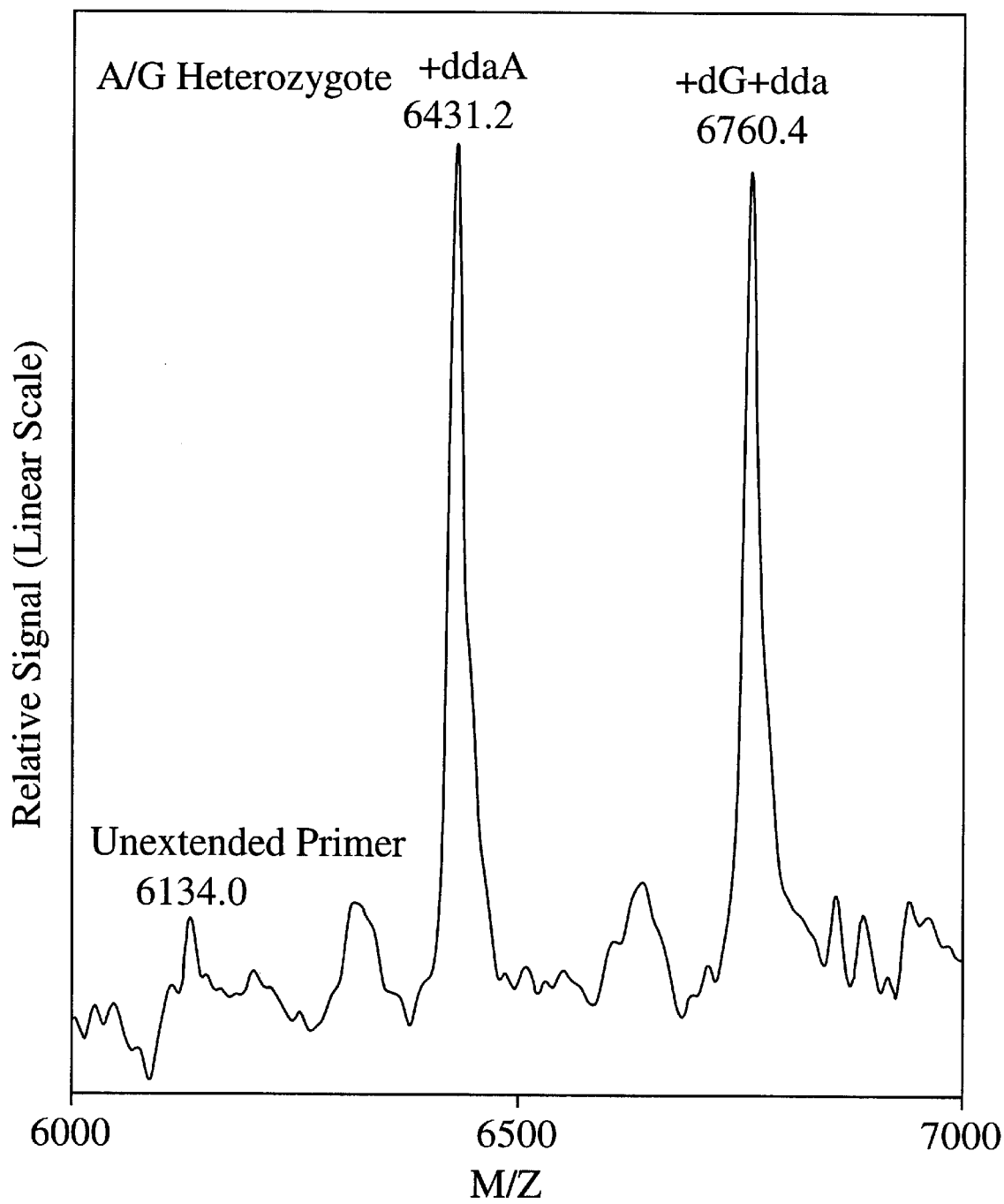
FIG. 7 MALDI-TOF mass spectrum of the extension products from an individual as described in Example 6, which were produced from an individual of A/G heterozygote.

FIG. 7 displays a mass spectrum of the extension products obtained from Person 20. Unlike FIGS. 5 and 6, FIG. 7 contains two product peaks. One peak corresponds to one-base extension product, while the other peak corresponds to two-base extension product. Thus person 20 is A/G heterozygous. Other people who were identified as A/G heterozygous produced similar spectra.

Nearly all of the 5 pmole of the mini-sequencing primers were converted to the extension products, even though the absolute amounts of the PCR products varied from sample to sample. The VSET assay is specific as evidenced by the absence of unexpected diagnostic peaks in the mass spectra.

Comparative Example A

For comparison, the PINPOINT method was also used to assay the same single nucleotide polymorphism site as in Example 3. However, for the PINPOINT assay, mini-sequencing was performed in the presence of all four ddNTPs, that is ddATP, ddCTP, ddGTP, and ddTTP. All other conditions and the DNA sample used were also the same as in Example 3. The results are shown in FIG. 4b.

Comparative Example B

For comparison, the PROBE method was also used to assay the same single nucleotide polymorphism site as in Example 3. However, for PROBE assay, mini-sequencing was performed in the presence of dATP, dCTP, dGTP and ddTTP. All other conditions and the DNA sample used were also the same as in Example 3.

Figure 3:
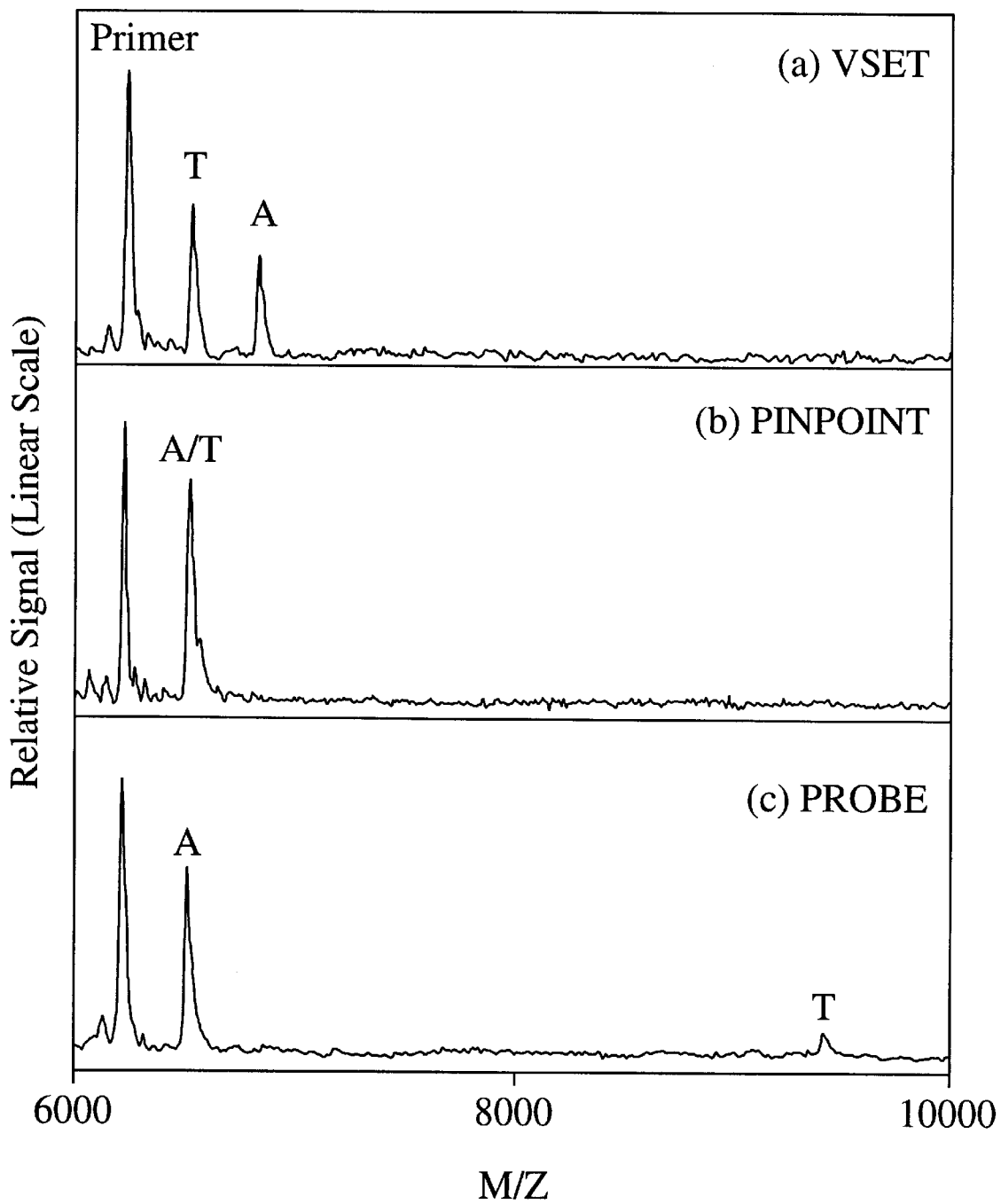

The results of genotyping an individual of A/T heterozygote (AJ243297/29366) according to Example 3, Comparative Example A, the PINPOINT method, Comparative Example B, and the PROBE method, were displayed in FIG. 3A, 3B and 3C, respectively. Two extension products were generated from Comparative Example A PINPOINT, where one allele led to one-base extension by adding ddA, while another also resulted in one-base extension by adding ddT. As shown in FIG. 3B these two extension products were poorly resolved and unassignable due to the small mass difference of 9 Da between ddA and ddT. In contrast, the A/T genotype was easily and unambiguously identified based on FIG. 3A since two extension products obtained from Example 3 differs by one base.

In Comparative Example B, the PROBE assay, the mini-sequencing primers were extended by 1 and 10 bases, respectively, for this A/T heterozygous sample. As shown in FIG. 3C the peak corresponding to 10-base extension products is barely discernible and its intensity was more than seven times weaker than that corresponding to one-base extension products. In contrast, two nucleotide extension products obtained from Example 3 yield comparable ion intensities.

Compared with Comparative Example A PINPOINT, Example 3 greatly relaxes the stringent mass resolution requirements since the bases at a single nucleotide polymorphism site are identified by examining the extension products to determine the number of nucleotides that have been added to the primers. This was achieved with minimal desalting, an ethanol precipitation step.

Compared with Comparative Example B, the PROBE assay, Example 3 leads to shorter extension products. As shown in FIG. 4C, long extension products in the Probe assay could lead to a major problem for multiplex genotyping since the extension efficiency varies significantly with the single nucleotide polymorphism sites and samples; some of the single nucleotide polymorphism samples will be well extended, while others may be poorly extended. As a result, long extension products may not be observable as mass spectrometric peaks if extension is poor.

Therefore, in the method of comparative Example B a heterozygous genotype could be mistakenly assigned as homozygote. Other problems associated with long extension include overlapping of long extension products with the products from other single nucleotide polymorphism sites; and overlapping double-charged and dimer ions with singly charged monomer ions.

What is claimed is:

1. A method for determining a nucleotide in a polynucleotide, comprising the following steps:
   a. providing a polynucleotide comprising at least one target site, and a first region of nucleotides immediately adjacent to the target site;
   b. then combining the polynucleotide with:
      a minisequencing primer complementary to the first region of nucleotides;
      three dideoxynucletides selected from the group consisting of ddATP, ddCTP, ddTTP and ddGTP;
      a deoxynucleotide selected from the group consisting of dATP, dCTP, dTTP and dGTP;
      wherein the nucleotide of the deoxynucleotide is not the same as the nucleotide in the dideoxynulceotide; and
   c. then extending the mini-sequencing primer with dideoxynucletide or deoxynulceotide whose base is complementary to the base at the target site, to provide extension products; and
   d. then analyzing the extension products with mass spectrometry.

2. The method of claim 1, wherein the polynucleotide is amplified before step b.

3. The method of claim 1, further comprising the step of desalting after mini-sequencing.

4. The method of claim 1, wherein the nucleotide polymorphism is a single nucleotide polymorphism.

5. The method of claim 4, wherein the single nucleotide polymorphism is 1691$^{th}$ base of the coagulation Factor V gene.

6. The method of claim 1, wherein the mass spectrometry is matrix-assisted laser-desorption/ionization time-of-flight mass spectrometry.

7. A method for determining a nucleotide in a single nucleotide polymorphism, comprising the following steps:
   a. providing a polynucleotide comprising at least one single nucleotide polymorphism site, and a first region of nucleotides immediately adjacent to the polymorphism site;
   b. then combining the polynucleotide with:
      a minisequencing primer which is complementary to the first nucleotide region;
      three different dideoxynucletides selected from the group consisting of ddATP, ddCTP, ddTTP and ddGTP;
      a deoxynucleotide selected from the group consisting of dATP, dCTP, dTTP and dGTP;
      wherein the nucleotide of the deoxynucleotide is not the same as the nucleotide in the dideoxynulceotide; and
   c. extending the mini-sequencing primer with dideoxynucletide or deoxynulceotide whose base is complementary to the base at the single nucleotide polymorphism site, to provide extension products; and
   d. analyzing the extension products with mass spectrometry.

8. The method of claim 7, wherein the polynucleotide is amplified before step b.

9. The method of claim 8, wherein the amplification is by polymerase chain reaction, and the unreacted deoxynucleotides and primers are removed after amplification.

10. The method of claim 7, further comprising the step of desalting after mini-sequencing.

11. The method of claim 10, wherein the desalting is done by ethanol purification.

12. The method of claim 8, wherein the nucleotide polymorphism is a single nucleotide polymorphism.

13. The method of claim 12, wherein the polynucleotide further comprises a second single polymorphism site.

14. The method of claim 7, wherein the mass spectrometry is Matrix-assisted laser-desorption/ionization time-of-flight mass spectrometry.

15. The method of claim 7, wherein the polynucleotide is amplified by polymerase chain reaction before step b, the single nucleotide polymorphism is 1691$^{th}$ base of the coagulation Factor V gene, the mass spectrometry is Matrix-assisted laser-desorption/ionization time-of-flight mass spectrometry.

16. A method for determining the nucleotides in multiple nucleotide polymorphism sites, comprising the following steps:
   a. providing a polynucleotide sample comprising:
      a first polynucleotide comprising at least one single nucleotide polymorphism site, and a first region of nucleotides immediately adjacent to the polymorphism site;
      a second polynucleotide comprising at least one single nucleotide polymorphism site, and a second region of nucleotides immediately adjacent to the polymorphism site;

b. then combining the polynucleotide sample with:
   a first minisequencing primer which is complementary to the first nucleotide region;
   a second minisequencing primer which is complementary to the second nucleotide region;
   three different dideoxynucletides selected from the group consisting of ddATP, ddCTP, ddTTP and ddGTP;
   a deoxynucleotide selected from the group consisting of dATP, dCTP, dTTP and dGTP;
   wherein the nucleotide of the deoxynucleotide is not the same as the nucleotide in the dideoxynulceotide; and
c. extending the mini-sequencing primer with a dideoxynucletide or deoxynulceotide whose base is complementary to the base at the single nucleotide polymorphism site, to provide extension products; and
d. analyzing the extension products with mass spectrometry.

17. The method of claim 16, wherein the polynucleotide sample is amplified before step b.

18. The method of claim 17, wherein the amplification is by polymerase chain reaction.

19. The method of claim 18, wherein unreacted dideoxynucleotides and primers are removed after amplification.

20. The method of claim 17, further comprising the step of desalting after mini-sequencing.

21. The method of claim 20, wherein the desalting is done by ethanol purification.

22. The method of claim 16, wherein the nucleotide polymorphism is a single nucleotide polymorphism.

23. The method of claim 16, wherein the single nucleotide polymorphism is $1691^{th}$ base of the coagulation Factor V gene.

24. The method of claim 16, wherein the mass spectrometry is matrix-assisted laser-desorption/ionization time-of-flight the mass spectrometry.

25. The method of claim 17, wherein the polynucleotides are amplified together.

26. The method of claim 17, wherein the polynucleotides are amplified separately, then the amplified polynucleotides are pooled prior to step c.

27. The method of claim 1, wherein the mini-sequencing primers are at least 5 nucleotide bases in length.

* * * * *

UNITED STATES PATENT AND TRADEMARK OFFICE
CERTIFICATE OF CORRECTION

PATENT NO.    : 6,479,242 B1
DATED         : November 12, 2002
INVENTOR(S)   : Guo et al.

It is certified that error appears in the above-identified patent and that said Letters Patent is hereby corrected as shown below:

<u>Title page,</u>
Item [22], Filed, please delete "October 27, 2000" and insert -- October 26, 2000 --

Signed and Sealed this

Twenty-fifth Day of March, 2003

JAMES E. ROGAN
*Director of the United States Patent and Trademark Office*